United States Patent
Nakao

(10) Patent No.: US 6,234,632 B1
(45) Date of Patent: May 22, 2001

(54) CORNEA SHAPE MEASURING APPARATUS

(75) Inventor: Hirohisa Nakao, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 09/549,547

(22) Filed: Apr. 14, 2000

(30) Foreign Application Priority Data

Apr. 16, 1999 (JP) ................................. 11-109216

(51) Int. Cl.⁷ .................................................. A61B 3/10
(52) U.S. Cl. ............................................................ 351/212
(58) Field of Search ................................. 351/205, 211, 351/212, 208, 221, 246; 606/4, 5

(56) References Cited

U.S. PATENT DOCUMENTS

| 5,751,396 | * | 5/1998 | Masuda et al. | 351/221 |
| 5,870,167 | * | 2/1999 | Knopp et al. | 351/212 |
| 5,909,270 | * | 6/1999 | Moser et al. | 351/212 |

FOREIGN PATENT DOCUMENTS 8-98802   4/1996   (JP) .

* cited by examiner

*Primary Examiner*—George Manuel
(74) *Attorney, Agent, or Firm*—Armstrong, Westerman, Hattori, McLeland & Naughton, LLP

(57) ABSTRACT

A cornea shape measuring instrument is provided which displays a superimposed image obtained by superimposing an anterior ocular segment image on a cornea refractive power distribution image and with which an operator can grasp with reality the positional relationship between the cornea refractive power distribution and the eye to be examined. Anterior ocular segment image data including ring pattern image data obtained by an optical measurement unit 100 is stored in an image memory 9. An control circuit 10 calculates the cornea refractive power distribution based on the ring pattern image data. The cornea refractive power distribution data representing the cornea refractive power distribution is stored in the refractive power distribution data memory 11. Further, the control circuit 10 carries out pixel-skipping process on the cornea refractive power distribution data based on mask pattern data stored in a mask pattern memory 12, and carries out image processing so that an anterior ocular segment image looks transparent. The superimposed image data obtained by superimposing the cornea refractive power distribution data and the anterior ocular segment image data is stored in a superimposed image memory 13 and is displayed on a display unit 300.

9 Claims, 5 Drawing Sheets

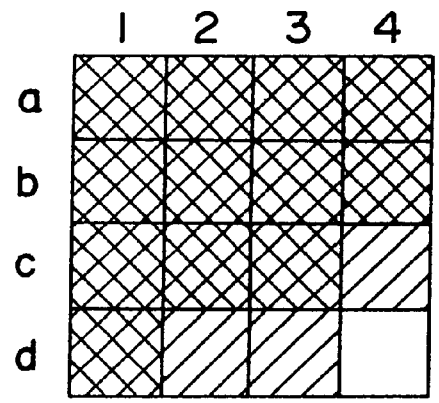
FIG. 5a
FIG. 5b
| | 1 | 2 | 3 | 4 |
|---|---|---|---|---|
| a | O | O | O | 1 |
| b | O | O | O | 1 |
| c | 1 | O | O | O |
| d | 1 | O | O | O |
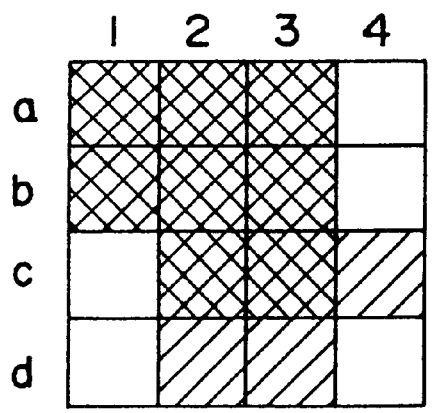
FIG. 5c

CORNEA SHAPE MEASURING APPARATUS

BACKGROUND OF THE INVENTION

1. Field of the Invention

The present invention relates to a cornea shape measuring instrument for measuring the shape of a cornea of a subject's eye for optometry in ophthalmological clinics, optician's shops, or the like.

2. Description of the Related Art

Conventionally, an instrument is known which projects a plurality of concentric ring-shaped targets toward a cornea of a subject's eye, and measures the distribution of the cornea refractive power by analyzing the shape of an image reflected by the cornea. The results of the measurements are output by a printer or the like. The results of the measurements output by the printer are used in optician's shops as prescription data for contact lens, or in ophthalmological clinics as data for orthokeratology.

Japanese Patent Application Laid-open No. Hei 8-98802 discloses an instrument that the refractive power distribution map of the cornea (hereinafter, simply referred to as "a distribution map") in relation to the position of the pupil and the cornea, thereby making it possible to easily understand the positional relationship between the distribution map and the pupil or the cornea.

By the way, in the instrument disclosed in Japanese Patent Application Laid Open No. Hei 8-98802, as illustrated in FIG. 1, circular figures which designate the shape of the pupil image Ep's or that of the cornea margin image Ei' are generated by image recognition process, and these figures are superimposed on the distribution map. Therefore, an operator can correctly understand the positional relationship between the distribution map and the eye by referring to the superimposed image displayed on the display unit. However, since an anterior ocular segment image itself is not displayed on the display unit, there is a problem that the operator can not grasp with reality the positional relationship.

SUMMARY OF THE INVENTION

The present invention has been made in view of the above, and therefore has an object to provide a cornea shape measuring instrument which displays a superimposed image obtained by superimposing an anterior ocular segment image on a distribution map image and with which an operator can grasp with reality the positional relationship between the distribution map and the subject's eye.

In order to solve the above problem, according to one aspect of the present invention, there is provided a cornea shape measuring instrument characterized by comprising: obtaining means for obtaining anterior ocular segment image data and distribution data concerning cornea refractive power of a subject's eye; storing means for storing pixel- skipping data for skipping the distribution data; pixel-skipping means for skipping the distribution data based on the pixel-skipping data; and means for displaying the distribution data and the anterior ocular segment image data in superimposed display state.

In order to solve the above problem, according to another aspect of the present invention, there is provided a cornea shape measuring instrument characterized by comprising: obtaining means for obtaining anterior ocular segment image data and distribution data concerning cornea refractive power of a subject's eye; storing means for storing pixel-skipping data for skipping the anterior ocular segment image data; pixel-skipping means for skipping the anterior ocular image data based on the pixel-skipping data; and means for displaying the anterior ocular image data and the distribution data in superimposed display state.

BRIEF DESCRIPTION OF THE DRAWINGS

In the accompanying drawings:

FIGS. 5A to 5C explain the skipping process in an arithmetic unit of the cornea shape measuring instrument according to the embodiment of the present invention.

DETAILED DESCRIPTION OF THE PREFERRED EMBODIMENTS

An embodiment of the present invention is now described with reference to the drawings.

Figure 1:
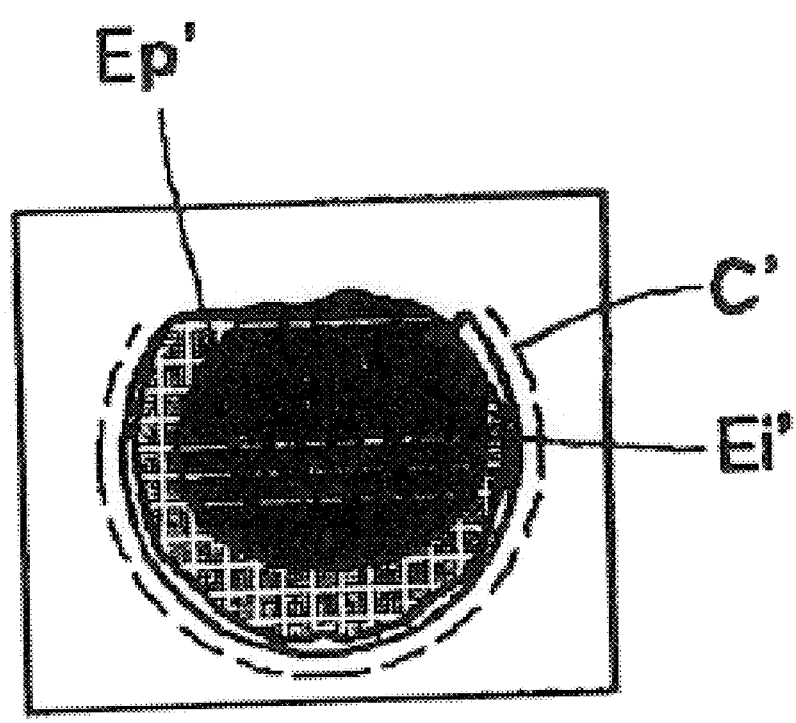
FIG. 1 illustrates an example of an image displayed on a display unit of a conventional cornea shape measuring instrument.
Figure 2:
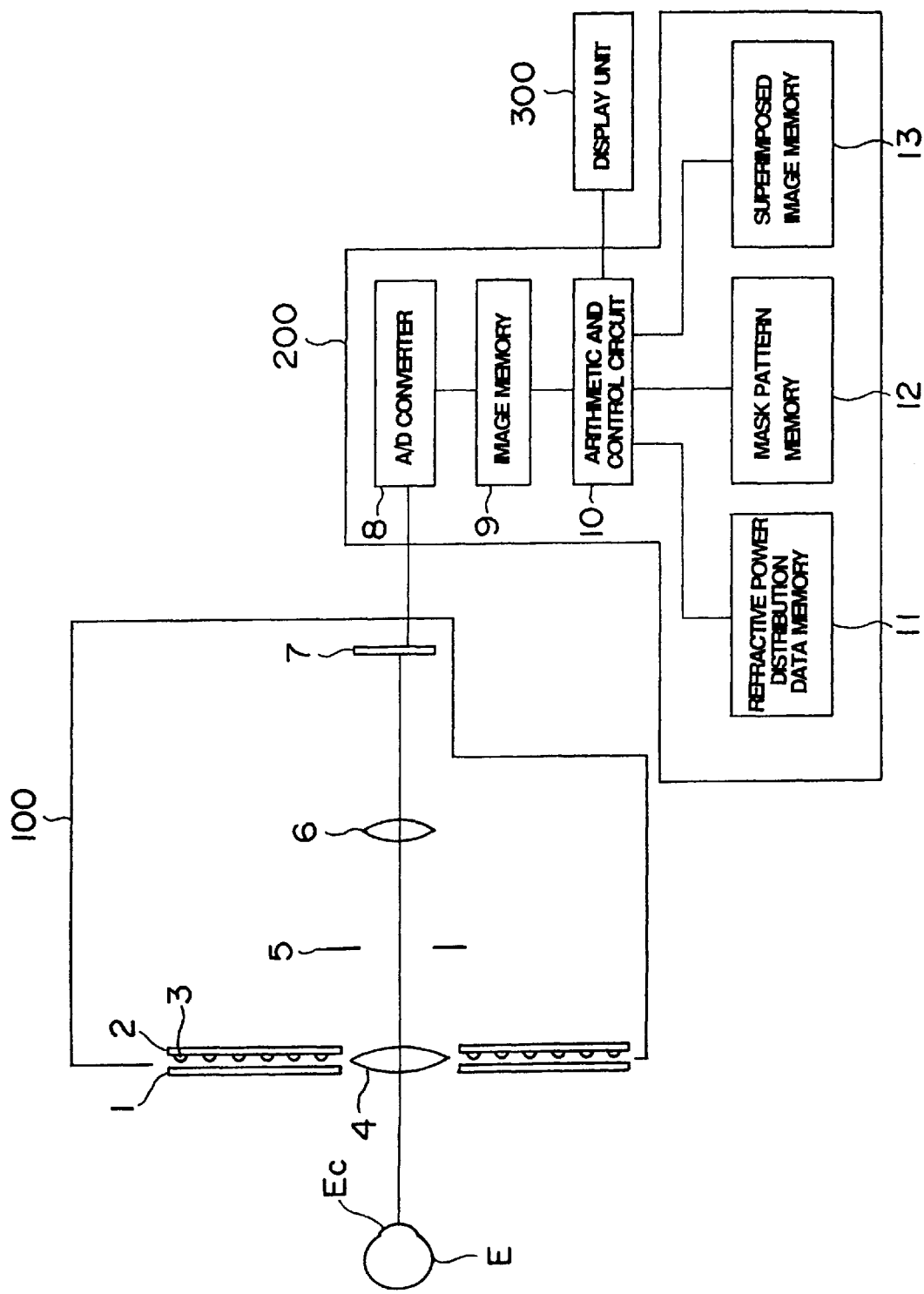
FIG. 2 illustrates the structure of a cornea shape measuring instrument according to an embodiment of the present invention.

FIG. 2 illustrates the structure of a cornea shape measuring instrument according to an embodiment of the present invention. The cornea shape measuring instrument as an embodiment of the present invention shown in FIG. 2 comprises an optical measurement unit 100 for housing an optical system for obtaining optical information with regard to anterior ocular segment image data and cornea refractive power distribution graphic pattern data (hereinafter referred to as distribution map) forming the cornea refractive power distribution of the eye E, an arithmetic unit 200 for processing the anterior ocular segment image data and the cornea refractive power distribution data, and superimposing the data to obtain a superimposed image, and a display unit 300 for displaying the superimposed image obtained by the arithmetic unit 200.

The optical measurement unit 100 is composed of a Placido's disk 1 having a Placido's pattern formed thereon for measuring the shape of a cornea Ec of the eye E, a Placido's lighting system 2 having a plurality of light-emitting diodes (LEDs) 3 for projecting the Placido's pattern formed on the Placido's disk 1 on the eye E, an objective 4, a diaphragm 5, an imaging lens 6 and a charge-coupled device (CCD) 7.

The Placido's disk 1 has a light scattering plate (not shown) having a transparent portions whose shape is Placido's pattern (a plurality of concentric ring-shaped pattern).

By irradiating the Placido's disk 1 with the plurality of LEDs 3, the Placido's pattern is projected toward the eye E. The anterior ocular segment of the eye E is irradiated by an anterior ocular segment light source (not shown), and anterior ocular segment observation light flux is projected toward the eye E.

The Placido's pattern and the anterior ocular segment observation light flux reflected by the eye E pass through the objective 4, the diaphragm 5, and the imaging lens 6, and an anterior ocular segment image including the ring pattern image is formed on the CCD 7.

The arithmetic unit 200 is formed of an analog/digital (A/D) converter 8, an image memory 9, an control circuit 10, a refractive power distribution data memory 11, a mask pattern memory 12, and a superimposed image memory 13.

The A/D converter 8 converts image signals output from the CCD 7 into digital signals representing coordinate positions and the brightness thereof. The digital signals converted by the A/D converter 8 are stored in the image memory 9 as anterior ocular segment image data including ring pattern image data.

The control circuit 10 extracts the ring pattern image data from the anterior ocular segment image data stored in the image memory 9 and calculates the cornea refractive power distribution based on the extracted ring pattern image data to obtain a distribution map. The cornea refractive power distribution data are stored in the refractive power distribution data memory 11.

When obtaining a superimposed image data by superimposing the distribution map data and the anterior ocular segment image data, the control circuit 10 carries out image processing so as to skip predetermined pixels in the distribution map, based on the mask pattern data as pixel-skipping data which are stored in advance in the mask pattern memory 12, whereby the anterior ocular segment image displayed on the display unit 300 looks translucent.

The superimposed image data is stored in the superimposed image memory 13 and is displayed on the display unit 300.

Next, operation of the cornea shape measuring instrument according to an embodiment of the present invention is described.

Figure 3:
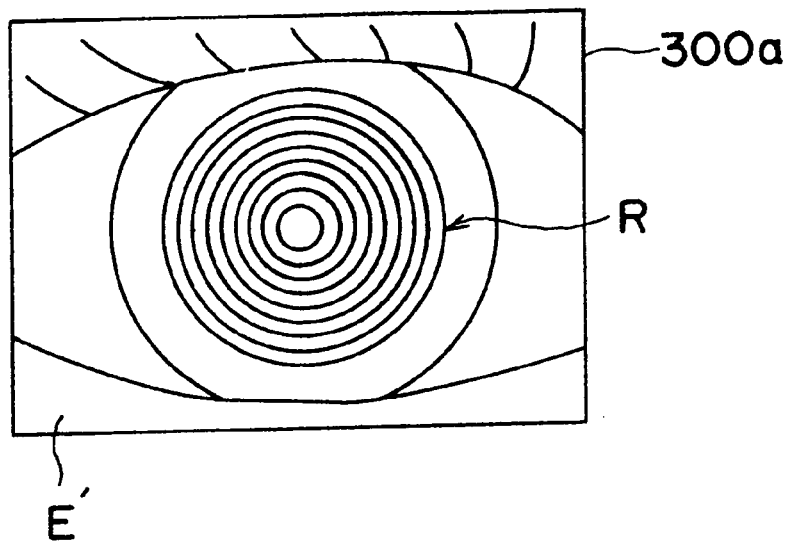
FIG. 3 illustrates an anterior ocular segment image and a ring pattern image displayed on a display unit of the cornea shape measuring instrument according to the embodiment of the present invention.

When the anterior ocular segment portion of the eye E is irradiated by the anterior ocular segment lighting light source (not shown), and an anterior ocular segment image E' is displayed on a display screen 300a of the display unit 300 as illustrated in FIG. 3, the operator aligns the optical measurement unit 100 with the eye E, observing the anterior ocular segment image E'. After that, a measurement start switch is pressed to make the Placido's lighting system 2 emit light, which makes the ring pattern light flux projected on the cornea Ec of the eye E. The ring pattern light flux reflected by the cornea pass through the objective 4, the diaphragm 5, and the imaging lens 6, and an image is formed on the CCD 7.

Picture signals output from the CCD 7 is converted by the A/D converter 8 into digital signals, and then, is stored in the image memory 9 as the anterior ocular segment image data including the ring pattern image data. The control circuit 10 makes Placiso's pattern image R corresponding to the ring pattern image data stored in the image memory 9 displayed on the display screen 300a of the display unit 300 as illustrated in FIG. 3.

Figure 4:
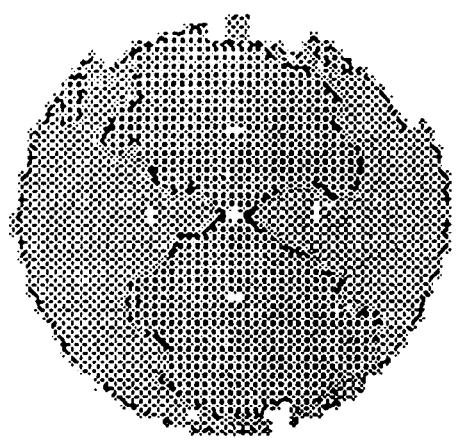
FIG. 4 illustrates the distribution map of the cornea refractive power displayed on a display screen of the display unit of the cornea shape measuring instrument according to the embodiment of the present invention.

Further, the control circuit 10 extracts the Placido's pattern image data from the anterior ocular segment image data stored in the image memory 9 and calculates the cornea refractive power distribution based on the Placido's pattern image data. The cornea refractive power distribution data representing the calculated cornea refractive power distribution is stored in the refractive power distribution data memory 11. It is to be noted that FIG. 4 illustrates an example of the distribution map displayed on the display unit 300 based on the cornea refractive power distribution data.

Still further, when the superimposed image data is obtained by superimposing the distribution map data on the anterior ocular segment image data, the control circuit 10 skips predetermined pixels in the distribution map data based on the mask pattern data which is stored in the mask pattern memory 12. It is to be noted that when the distribution map data and the anterior ocular segment image data overlap in a pixel which is not skipped, the distribution map data has priority over the anterior ocular segment image data and are displayed on the display unit 300.

It is to be noted that mask pattern data representing a mask pattern of 4×4 pixels as illustrated as an example in FIG. 5b, are stored in the mask pattern memory 12. The mask pattern data are used as data for determining whether the cornea distribution map data read out from the refractive power distribution data memory 11 should be written in the superimposed image memory 13 with regard to each pixel or not.

More specifically, the mask pattern data stored in the mask pattern memory 12 numerically show which pixels of the distribution map data are to be skipped. For example, as shown in FIG. 5b, when the value of a pixel in the mask pattern data is "1", the distribution map data corresponding to the pixel is skipped. On the other hand, when the value of a pixel in the mask pattern data is "0", the distribution map data corresponding to the pixel remains as it is.

Therefore, when the value of a pixel is "1", not the distribution map datum but the anterior ocular segment image datum corresponding to the pixel is used for the pixel of the superimposed image. On the other hand, when the value of a pixel is "0", not the anterior ocular segment image datum but the distribution datum corresponding to the pixel is used for the pixel of the superimposed image.

For example, in FIG. 5b, since the values of pixels (1,*c*), (1,*d*), (4,*a*), and (4,*b*) are "1", the distribution map data corresponding to these pixels (see FIG. 5a) are skipped, and are not written in the corresponding storage regions of the superimposed image memory 13. Instead, the corresponding anterior ocular segment data are allocated to the pixels (1,*c*), (1,*d*), (4,*a*), and (4,*b*) to be written in the corresponding storage regions of the superimposed image memory 13.

On the other hand, since the values of pixels other than the pixels (1,*c*), (1,*d*), (4,*a*), and (4,*b*) are "0", the distribution map data corresponding to these pixels are not skipped, and are written as they are in the corresponding storage regions of the superimposed image memory 13.

Figure 6:
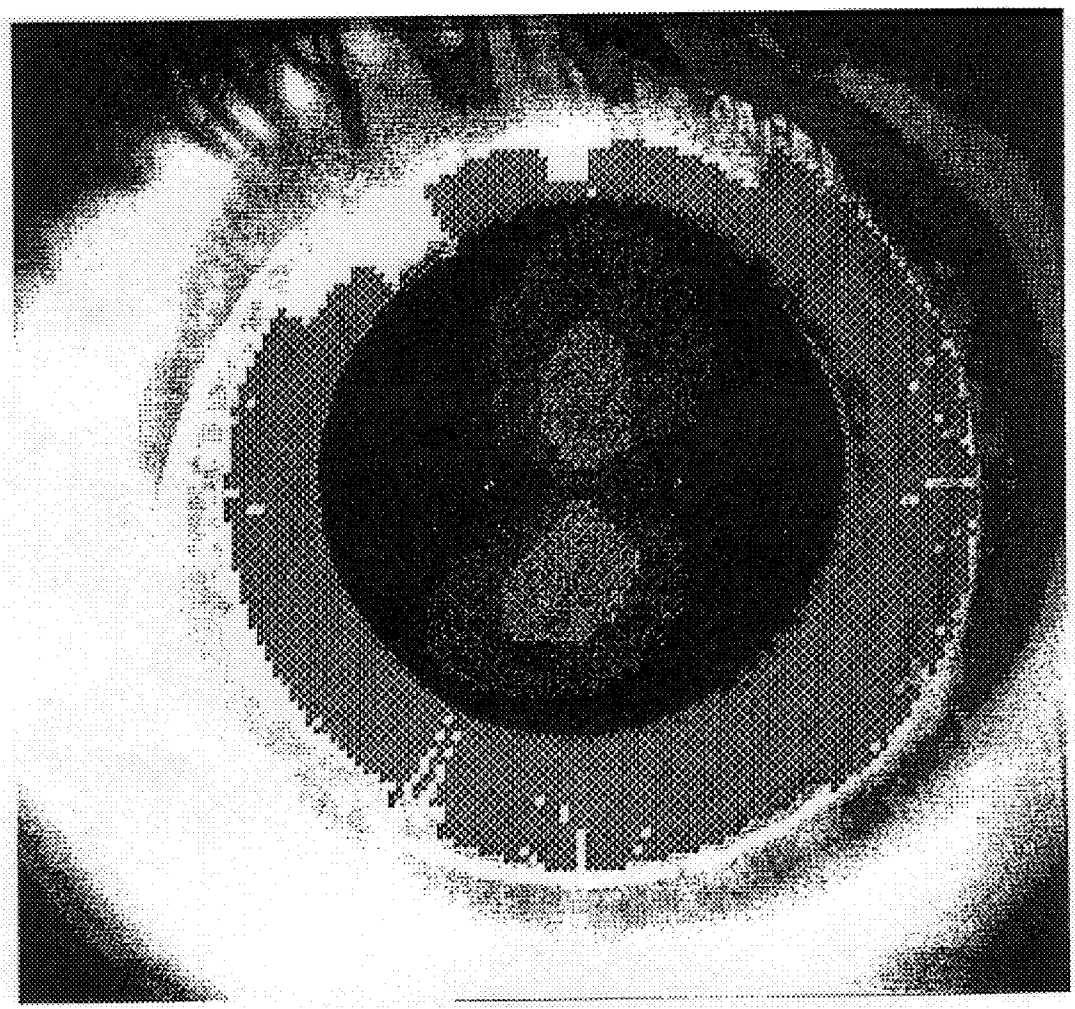
FIG. 6 illustrates an example of a superimposed image displayed on the display unit of the cornea shape measuring instrument according to the embodiment of the present invention.

By the skipping process described in the above, a superimposed image as illustrated in FIG. 5c is written in the superimposed image memory 13. It is to be noted that, in FIG. 5c, shaded pixels and screened pixels denote the distribution map data while the remaining white pixels denote anterior ocular segment image data. Since the distribution map data and the anterior ocular segment image data are mixed in a certain ratio in the superimposed image displayed on the display unit 300, the anterior ocular segment image looks translucent. FIG. 6 illustrates an example of a superimposed image displayed on the display unit 300. It is to be noted that such a superimposed image illustrated in FIG. 6 can be printed out by a printer unit that is not shown.

When a display unit of an interlace system is used and the (m)th pixel of the (2n−1)th (odd number) scanning line is skipped, the (m)th pixel of the (2n)th (even number) scanning line is also skipped. This prevents flicker of the display screen 300a of the display unit 300.

In the embodiment described above, after the operator presses the measurement start switch and ends the measurement of the cornea refractive power distribution, the distribution map is a subject of pixel-skipping process and is superimposed on the anterior ocular segment image, and the superimposed image is automatically displayed on the display unit. However, the present invention is not limited thereto. For example, it may be possible that, after the measurement of the cornea refractive power distribution ends, the anterior ocular segment image and the radius of curvature of the center portion of the cornea of the subject's eye are only numerically displayed on the display unit, and after that, when the operator presses a display change switch, the distribution map takes pixel-skipping process to be superimposed on the anterior ocular segment image, and the superimposed image is displayed on the display unit.

Further, in the embodiment described above, the cornea refractive power distribution data is the subject of the pixel-skipping process, and the anterior ocular segment image data is allocated to the corresponding skipped pixels. However, it is also possible that, conversely, the anterior ocular segment image data is the subject of the pixel-skipping process, and the cornea refractive power distribution data is allocated to the corresponding skipped pixels, and the superimposed image is displayed on the display unit.

Still further, the size of the mask pattern data stored in the mask pattern memory is not limited to 4×4 pixels. Mask pattern data of 8×8 pixels, 16×16 pixels, and the like may be used.

As described above, according to the present invention, since the anterior ocular segment image is superimposed on the distribution map displayed so as to be translucent, the operator can grasp very clearly the positional relationship between the distribution map and the subject's eye.

Further, since, when the display unit of the interlace system is used and the (m)th pixel of the (2n−1)th scanning line is skipped, the (m)th pixel of the (2n)th scanning line is also skipped, flicker of the display screen of the display unit can be prevented.

What is claimed is:

1. A cornea shape measuring instrument comprising:
   obtaining means for obtaining anterior ocular segment image data of a subject's eye and distribution data concerning cornea refractive power;
   storing means for storing pixel-skipping data for skipping the distribution data;
   pixel-skipping means for skipping the distribution data based on the pixel-skipping data; and
   means for displaying the distribution data and the anterior ocular segment image data in superimposed display state.

2. A cornea shape measuring instrument as claimed in claim 1, wherein said pixel-skipping means carries out image processing so as to skip predetermined pixels in the distribution data so that the anterior ocular segment image looks translucent when displaying means displays the superimposed image.

3. A cornea shape measuring instrument as claimed in claim 1, wherein said pixel-skipping means processes a predetermined pixel of the distribution data using a mask pattern memory in which mask pattern data to be used as the pixel-skipping data is previously stored.

4. A cornea shape measuring instrument as claimed in claim 3, wherein the mask pattern data stored in said mask pattern memory are defined by numerical value of "1" or "0".

5. A cornea shape measuring instrument comprising:
   obtaining means for obtaining anterior ocular segment image data and distribution data concerning cornea refractive power of a subject's eye;
   storing means for storing pixel-skipping data for skipping the anterior ocular segment image data;
   pixel-skipping means for skipping the anterior ocular image data based on the pixel-skipping data; and
   means for displaying the anterior ocular image data and the distribution data in superimposed display state.

6. A cornea shape measuring instrument as claimed in claim 5, wherein said pixel-skipping means carries out image processing so as to skip predetermined pixels in the anterior ocular image data so that the distribution image looks translucent when said displaying means displays the superimposed image.

7. A cornea shape measuring instrument as claimed in claim 5, wherein said pixel-skipping means processes a predetermined pixel of the anterior ocular segment image data using a mask pattern memory in which mask pattern data to be used as the pixel-skipping data is previously stored.

8. A cornea shape measuring instrument as claimed in claim 7, wherein the mask pattern data stored in said mask pattern memory are defined by numerical value of "1" or "0".

9. A cornea shape measuring instrument as claimed in claim 1 or 5, wherein when said displaying means is an interlace system (interlace scanning), said pixel-skipping means skips the (m)th pixel of the (2n)th scanning line together with the (m)th pixel the (2n−1)th scanning line.

* * * * *